US011844361B2

(12) United States Patent
Schmidt

(10) Patent No.: US 11,844,361 B2
(45) Date of Patent: Dec. 19, 2023

(54) STEM CELL BOOSTING CHOCOLATE COMPOSITION

(71) Applicant: WIPARO BIOMED LIMITED, Galway (IE)

(72) Inventor: David Schmidt, Winter Park, FL (US)

(73) Assignee: WIPARO BIOMED LIMITED, Galway (IE)

( * ) Notice: Subject to any disclaimer, the term of this patent is extended or adjusted under 35 U.S.C. 154(b) by 267 days.

(21) Appl. No.: 17/226,030

(22) Filed: Apr. 8, 2021

(65) Prior Publication Data

US 2022/0322692 A1 Oct. 13, 2022

(51) Int. Cl.

| | |
|---|---|
| *A61K 36/06* | (2006.01) |
| *A23G 1/48* | (2006.01) |
| *A61K 36/185* | (2006.01) |
| *A61K 9/00* | (2006.01) |
| *A23G 1/46* | (2006.01) |
| *A61K 36/15* | (2006.01) |
| *A61K 9/20* | (2006.01) |
| *A23G 1/42* | (2006.01) |

(52) U.S. Cl.
CPC .............. *A23G 1/48* (2013.01); *A23G 1/426* (2013.01); *A23G 1/46* (2013.01); *A61K 9/0056* (2013.01); *A61K 9/2018* (2013.01); *A61K 36/06* (2013.01); *A61K 36/15* (2013.01); *A61K 36/185* (2013.01)

(58) Field of Classification Search
None
See application file for complete search history.

(56) References Cited

U.S. PATENT DOCUMENTS

| | | | |
|---|---|---|---|
| 10,080,736 B2 | 9/2018 | Kleidon et al. | |
| 10,821,069 B2 | 11/2020 | Portolan et al. | |
| 2016/0166602 A1 | 6/2016 | Sands | |
| 2020/0146971 A1 | 5/2020 | Coquet et al. | |

FOREIGN PATENT DOCUMENTS

| | | | | |
|---|---|---|---|---|
| JP | 2006265219 A | * | 10/2006 | |
| WO | WO-2008127827 A1 | * | 10/2008 | ............... A23G 1/32 |
| WO | 2013133903 A1 | | 9/2013 | |
| WO | 2017218846 A1 | | 12/2017 | |

OTHER PUBLICATIONS

Guggenheim, et al., "Immune Modulation From Five Major Mushrooms: Application to Integrative Oncology," Integrative Medicine, vol. 13, No. 1; Feb. 2014 (13 pages).
Katz, et al., "Cocoa and Chocolate in Human Health and Disease," Antioxidants and Redox Signalling, vol. 15, No. 10 (2011); 34 pages.
Shoae-Hassani, et al., "DHEA provides a microenvironment for endometrial stem cells neurogenesis," Medical Hypotheses, vol. 76, Issue 6 (Jun. 2011); pp. 843-846.
Carter, et al., "What are the benefits of lion's mane mushrooms?", MedicalNewsToday; Mar. 19, 2021 (9 pages).
Kim, Yeon-Ran, "Immunomodulatory Activity of the Water Extract from Medicinal Mushroom *Inonotus obliquus*," Mycobiology 33(3; 158-162 (2005); The Korean Society of Mycology.
Heiss, et al., "Improvement of Endothelial Function With Dietary Flavanols Is Associated With Mobilization of Circulating Angiogenic Cells in Patients With Coronary Artery Disease," Journal of the American College of Cardiology (2010); 7 pages.
Kavanagh, Caroline, "Food is medicine, including dark chocolate!", retrieved on Mar. 16, 2021 from https://www.insideouthp.com/single-post/2019/10/11/food-is-medicine-including-dark-chocolate; 7 pages.

* cited by examiner

*Primary Examiner* — Susan T Tran
(74) *Attorney, Agent, or Firm* — ARC IP Law, PC; Joseph J. Mayo

(57) ABSTRACT

A composition for human consumption that combines various ingredients that boost stem cell activity. Illustrative ingredients may for example include high cacao content chocolate, medicinal mushroom extracts, substances containing or promoting DHEA, pine bark extract to convert arginine from cacao into nitric oxide to improve circulation. DHEA boosting substances may include truffle powder and/or pine pollen. An illustrative composition may have about 75% chocolate by weight, with cacao content of 73% or more, at least 10% truffle powder or pine pollen, at least 10% medicinal mushroom extracts, the remainder pine bark extract. The composition may be formulated into sublingual tablets of about 1 gram, and daily consumption may for example consist of 5 tablets for 5 grams total. Includes a method of supporting cardiovascular health, improving sexual performance and sexual health, and improving athletic performance by administering a therapeutic amount of the compound to a subject.

16 Claims, 2 Drawing Sheets

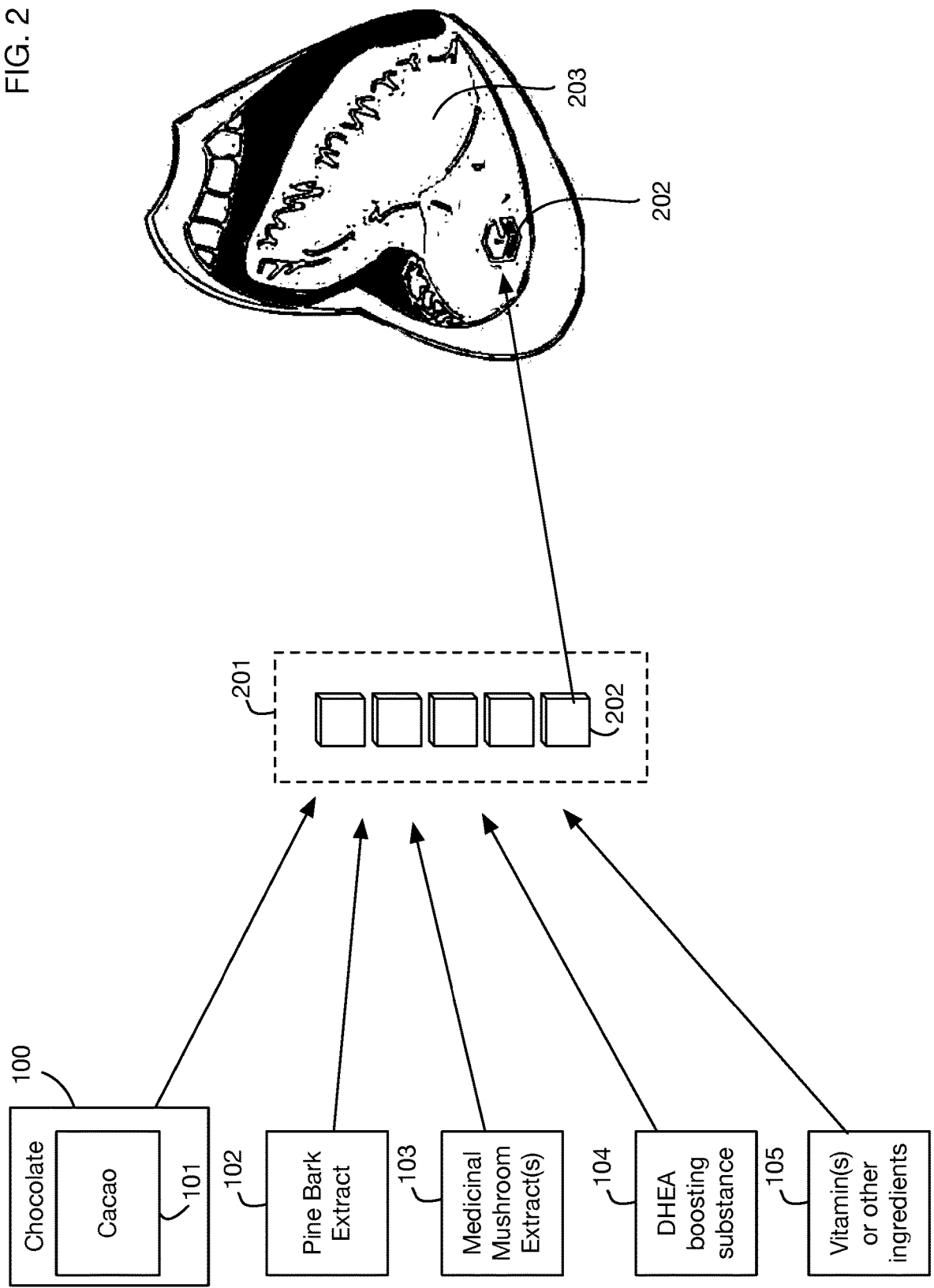

STEM CELL BOOSTING CHOCOLATE COMPOSITION

BACKGROUND OF THE INVENTION

Field of the Invention

One or more embodiments of the invention are related to the fields of health supplements and nutritional formulations. More particularly, but not by way of limitation, one or more embodiments of the invention enable a stem cell boosting chocolate composition.

Description of the Related Art

Several researchers have investigated the effect of various foods and supplements on stem cell activity and human health. Some substances that have been reported to have an effect on stem cell activity include cacao, medicinal mushrooms, and compounds that boost DHEA (dehydroepiandrosterone). For example, Heiss et. al. found a significant increase in stem cells after treating patients with high-flavanol cacao. (Christian Heiss, MD, et. al., "Improvement of Endothelial Function With Dietary Flavanols Is Associated With Mobilization of Circulating Angiogenic Cells in Patients With Coronary Artery Disease. 2017," *Journal The American College of Cardiology*, Vol. 56, No. 3, 2010.) Cacao, particularly in dark chocolate, has several potential health benefits (David L. Katz, Kim Doughty, and Ather Ali, "Cacao and Chocolate in Human Health and Disease", et. al. "Improvement of Endothelial Function With Dietary Flavanols Is Associated With Mobilization of Circulating Angiogenic Cells in Patients With Coronary Artery Disease. 2017." *Antioxidants & Redox Signaling*, Vol. 15, No. 10, 2011.) Medicinal mushrooms have been noted to affect hematopoietic stem cells, as well as lymphocytes, macrophages, T cells, dendritic cells, and natural killer cells (Alena G. Guggenheim, ND; Kirsten M. Wright, BS; Heather L. Zwickey, PhD, "Immune Modulation From Five Major Mushrooms: Application to Integrative Oncology," *Integrative Medicine*, Vol. 13, No. 1, February 2014.) DHEA has also been shown to improve neurogenesis from endometrial stem cells (Alireza Shoae-Hassani et. al., "DHEA provides a microenvironment for endometrial stem cells neurogenesis", *Medical Hypotheses*, Vol. 76, Issue 6, June 2011, pp. 843-846.)

Although each of these substances (cacao, medicinal mushrooms, and DHEA) have shown stem cell effects, compounds that combine these substances in effective proportions are not known in the art. For at least the limitations described above there is a need for a stem cell boosting chocolate composition.

BRIEF SUMMARY OF THE INVENTION

One or more embodiments described in the specification are related to a stem cell boosting chocolate composition. Embodiments of the invention may combine various ingredients with stem cell boosting effects, and potentially other health benefits, into a composition that may be consumed by a user, such as sublingually for example.

In one or more embodiments, the composition may include chocolate containing cacao, where the concentration by weight of cacao in the composition is at least 50% of the total weight of the composition. It may also include one or more DHEA boosting compounds in a concentration between 2% and 38% by weight of the total weight of the composition, and one or more mushroom extracts in a concentration between 2% and 38% by weight of the total weight of the composition.

One or more embodiments may include vitamin B12 in a concentration between 0.0001% and 5% by weight of the total weight of the composition.

In one or more embodiments, chocolate may be at least 70% by weight of the total weight of the composition. For example, in one or more embodiments the concentration of chocolate may be about 75% by weight of the total weight of the composition.

In one or more embodiments, the DHEA boosting compound(s) may include one or more of pine pollen and truffle powder.

In one or more embodiments, the chocolate may also contain sugar, vanilla, and soy lecithin.

In one or more embodiments, the composition may further include pine bark extract.

In one or more embodiments, some or all of the mushroom extracts may be extracts of one or more medicinal mushrooms. Illustrative medicinal mushrooms that may be used in one or more embodiments may include for example, without limitation, one or more of cordyceps, reishi, turkey tail, lion's mane, chaga, agarikon, maitake.

In one or more embodiments, chocolate may be at least 70% by weight of the total weight of the composition, and cacao may be between 60% and 90% by weight of the weight of the chocolate in the composition.

In one or more embodiments the concentration of cacao in the chocolate may be about 73% by weight of the weight of the chocolate.

In one or more embodiments, the chocolate may include cacao in a concentration by weight between 70% and 75% of the weight of the chocolate. The composition may include pine pollen in a concentration between 1% and 20% by weight of the total weight of the composition, cordyceps in a concentration between 1% and 20% by weight of the total weight of the composition, reishi in a concentration between 1% and 20% by weight of the total weight of the composition, and truffle powder in a concentration between 1% and 20% by weight of the total weight of the composition.

In one or more embodiments, chocolate may be at about 80% by weight of the total weight of the composition, and the chocolate may include cacao in a concentration by weight of about 75% of the weight of the chocolate. The composition may include pine pollen in a concentration of about 9.5% by weight of the total weight of the composition, cordyceps in a concentration of about 5% by weight of the total weight of the composition, reishi in a concentration of about 5% by weight of the total weight of the composition, and truffle powder in a concentration of about 0.5% by weight of the total weight of the composition.

In one or more embodiments, the composition may include pine pollen in a concentration between 1% and 20% by weight of the total weight of the composition, pine bark extract in a concentration between 1% and 20% by weight of the total weight of the composition, cordyceps in a concentration between 1% and 20% by weight of the total weight of the composition, reishi in a concentration between 1% and 20% by weight of the total weight of the composition, turkey tail in a concentration between 1% and 20% by weight of the total weight of the composition, lion's mane in a concentration between 1% and 20% by weight of the total weight of the composition, and truffle powder in a concentration between 1% and 20% by weight of the total weight of the composition.

In one or more embodiments, the composition may include chocolate in a concentration of at least 70% by weight of the total weight of the composition, and the chocolate may include cacao in a concentration by weight between 60% and 90% of the weight of the chocolate. The composition may include pine pollen in a concentration between 1% and 20% by weight of the total weight of the composition, pine bark extract in a concentration between 1% and 10% by weight of the total weight of the composition, cordyceps in a concentration between 1% and 20% by weight of the total weight of the composition, chaga in a concentration between 1% and 20% by weight of the total weight of the composition, truffle powder in a concentration between 1% and 20% by weight of the total weight of the composition, and vitamin B12 in a concentration between 0.01% and 5% by weight of the total weight of the composition.

In one or more embodiments, the composition may include chocolate in a concentration of about 75% by weight of the total weight of the composition, and the chocolate may include cacao in a concentration by weight of about 75% of the weight of the chocolate. The composition may include pine pollen in a concentration of about 10% by weight of the total weight of the composition, pine bark extract in a concentration of about 2% by weight of the total weight of the composition, cordyceps in a concentration of about 10% by weight of the total weight of the composition, chaga in a concentration of about 2.4% by weight of the total weight of the composition, truffle powder in a concentration of about 0.5% by weight of the total weight of the composition, and vitamin B12 in a concentration of about 0.1% by weight of the total weight of the composition.

BRIEF DESCRIPTION OF THE DRAWINGS

The above and other aspects, features and advantages of the invention will be more apparent from the following more particular description thereof, presented in conjunction with the following drawings wherein:

FIG. 2 shows an illustrative physical form for one or more embodiments: tablets of approximately 1 gram each that are consumed sublingually.

DETAILED DESCRIPTION OF THE INVENTION

Figure 1:
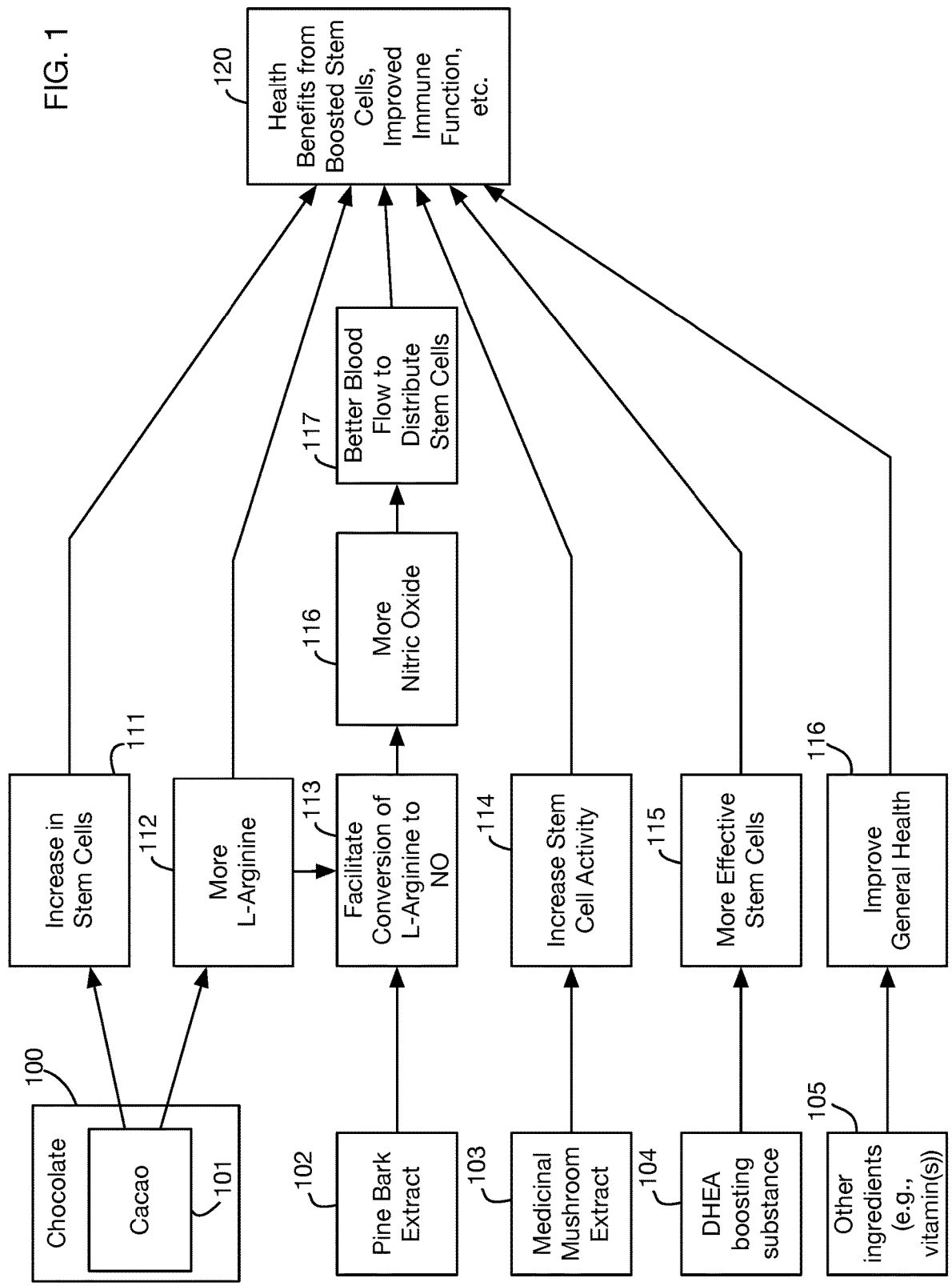
FIG. 1 shows illustrative substances that may be combined into one or more embodiments of the invention, and causal links between these substances and health benefits.

A stem cell boosting chocolate composition will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

One or more embodiments of the invention may combine substances with various beneficial effects on the human body into a consumable formulation. Potential benefits of such formulations may include, without limitation, increasing the number of stem cells in the body, increasing the effectiveness of those stem cells, improving blood flow in the body, and improving immune function. FIG. 1 illustrates some of the substances that may be present in one or more embodiments of the invention, and shows causal links between these substances and various factors that contribute to health benefits 120 from boosted stem cells and improved immune function. These factors are described below. One or more embodiments of the invention may include any or all of the substances shown in FIG. 1, or any subset of these substances.

It is well-known that as individuals age, the viability and activity of stem cells degrades. Boosting the number 111, activity 114, effectiveness 115, and distribution 117 of stem cells can therefore have significant health benefits 120. A study on cacao 101 demonstrated that it was capable of doubling the number of stem cells in the body, particularly with chocolate having a cacao content of at least 73%. In one or more embodiments of the invention, cacao 101 may be used for the purpose of increasing the number of stem cells 111 in the body. Cacao 101 may be part of chocolate 100; the chocolate may contain other ingredients in addition to cacao for flavor, texture, and consistency, or for other health benefits. In one or more embodiments, chocolate may be at least 70% by weight of the total weight of the composition. In one or more embodiments, the cacao in the chocolate may be at least 50% by weight of the total weight of the composition.

Other research has shown that the level of DHEA in the body may positively affect the effectiveness 115 of stem cells, causing these stem cells to act like younger, healthier cells. Therefore one or more embodiments may also include a DHEA boosting compound 104, such as either or both of pine pollen and truffle powder. These DHEA boosting compound(s) may either contain DHEA, or may induce the body to make or retain more DHEA. In one or more embodiments, the DHEA boosting compound(s) may be between 2% and 38% of the total weight of the composition.

In order to allow the boosted stem cells to travel thru the cardiovascular system it may be desirable to also include in one or more embodiments a natural ingredient that is known to elevate Nitric oxide (NO). NO is a vasodilator and is synthesized in the body from the amino acid L-Arginine. While cacao is a natural source of L-Arginine, it has previously been discovered that pine bark extract 102 will facilitate the conversion 113 of Arginine to NO 116. Therefore, another novel aspect of one or more embodiments of the invention is the formulation of cacao as a source of arginine 112 for the pine bark mediated conversion 113 to NO 116, resulting in better blood flow 117 to better distribution stem cells.

Further, it has been demonstrated that specific medicinal mushrooms 103 (such as cordyceps for example) have beneficial effects on the activity 114 of stem cells in the body, and this results in improvement of such things as immune function, energy and stamina. Therefore, one or more embodiments of the invention may also include one or more mushrooms or extracts from these mushrooms. Any mushroom or mushrooms may be used in one or more embodiments of the invention, including but not limited to mushrooms that are known or suspected to have potential health benefits. In one or more embodiments, the mushrooms or mushroom extracts may be between 2% and 38% of the total weight of the composition.

One or more embodiments of the invention may also include one or more other ingredients 105, such as ingredients that are known or suspected to improve general health 116 or that have any other stem cell effects. Such ingredients may for example include vitamins, such as vitamin B12 or other vitamins. Vitamin B12 in particular may improve the efficacy of nitric oxide, contributing to vasodilation induced by the nitric oxide generated by the conversion of L-Arginine in cacao to NO induced by pine bark extract. In one or more embodiments, the vitamin B12 may be between 0.0001% and 5% of the total weight of the composition.

FIG. 2 shows an illustrative physical embodiment of the invention that combines the ingredients chocolate 100 containing cacao 101, pine bark extract 102, medicinal mushroom extract 103, a DHEA boosting substance 104, and potentially one or more other ingredients 105 such as one or more vitamins. In this illustrative embodiment, the ingredients may be combined into tablets 201, each tablet weighing approximately 1 gram. Each tablet, such as tablet 202, may for example be placed under the tongue 203 so that it may dissolve, delivering the ingredients sublingually. This method of delivery may be superior to products intended to be absorbed via digestion. A daily serving may for example contain 5 tablets 201 measuring approximately 5 grams in total.

The inventor has experimented with a large number of ingredients and ingredient proportions to determine a combination that is effective and that has a pleasing taste and consistency. The inventor has discovered that there is a balance between the amount of efficacious compounds and the consistency of the end product; in particular, the more pine pollen, the more difficult it becomes for the end product to hold together. Also, a formulation with much less than 75% chocolate appears to be less desirable in terms of flavor and excessive brittleness of the product; therefore one or more embodiments may contain at least 70% chocolate (by weight). For the chocolate, the cacao content may be for example between 60% and 90% cacao (as a percentage of the total weight of the chocolate) in one or more embodiments. The chocolate might also contain for example, without limitation, sugar, vanilla, and lecithin, to enhance taste and consistency.

Illustrative DHEA boosting compounds that may be used in one or more embodiments may include for example, without limitation, either or both of truffle powder and pine pollen. Other DHEA boosting ingredients (that either contain DHEA or that increase production or retention of DHEA in the body) may be used in one or more embodiments.

One or more embodiments may use any type of mushrooms or mushroom extracts, particularly those mushrooms that have been shown to or are suspected of having health benefits such as enhancement of stem cell activity. Illustrative mushrooms that may be used may include for example, without limitation, one or more of cordyceps, reishi, turkey tail, lion's mane, chaga, agarikon, and maitake. Cordyceps may for example further improve stem cell function, and chaga may protect stem cells due to its SOD (superoxide dismutase) content.

One or more embodiments may contain additional ingredients, such as for example vitamins such as vitamin B12. In particular any ingredient or ingredients with known or suspected health benefits may be added to the composition.

The tables below list illustrative combinations of ingredients that may be used in one or more embodiments. Percentages shown are percentages by weight of the total product weight, which may be for example approximately 1 gram for an illustrative tablet. In some illustrative embodiments, percentages are shown as a range; specific embodiments may combine ingredients in any proportions within the given ranges.

TABLE 1

First Illustrative Embodiment

| Ingredient | Percentage |
| --- | --- |
| Chocolate, 77% cacao | 80% |
| Truffle powder | 10% |
| Mushroom powder, e.g., Lion's Mane | 10% |

TABLE 2

Second Illustrative Embodiment

| Ingredient | Percentage |
| --- | --- |
| Chocolate, 60% to 90% cacao | 70% or more |
| Pine Pollen | 1% to 20% |
| Pine Bark Extract | 1% to 10% |
| Cordyceps | 1% to 20% |
| Chaga | 1% to 20% |
| Truffle Powder | 1% to 20% |
| Vitamin B12 | 0.01% to 5% |

TABLE 3

Third Illustrative Embodiment

| Ingredient | Percentage |
| --- | --- |
| Chocolate, 75% cacao, sugar, vanilla, lecithin | 75% |
| Pine Pollen | 10% |
| Pine Bark Extract | 2% |
| Cordyceps | 10% |
| Chaga | 2.4% |
| Truffle Powder | 0.5% |
| Vitamin B12 | 0.1% |

TABLE 4

Fourth Illustrative Embodiment

| Ingredient | Percentage |
| --- | --- |
| Chocolate, 75% cacao | 60% |
| Pine Pollen or Truffle Powder | 30% |
| Cordyceps or Other Mushroom | 10% |

TABLE 5

Fifth Illustrative Embodiment

| Ingredient | Percentage |
| --- | --- |
| Chocolate, 75% cacao | 60% |
| Pine Pollen or Truffle Powder | 20% |
| Cordyceps or Other Mushroom | 20% |

TABLE 6

Sixth Illustrative Embodiment

| Ingredient | Percentage |
| --- | --- |
| Chocolate, 70% to 75% cacao, sugar, natural vanilla, soy lecithin | 70% or more |
| Pine Pollen | 1% to 20% |
| Cordyceps | 1% to 20% |

TABLE 6-continued

Sixth Illustrative Embodiment

| Ingredient | Percentage |
| --- | --- |
| Reishi | 1% to 20% |
| Truffle Powder | 1% to 20% |

TABLE 7

Seventh Illustrative Embodiment

| Ingredient | Percentage |
| --- | --- |
| Chocolate, 75% cacao, sugar, natural vanilla, soy lecithin | 80% |
| Pine Pollen | 9.5% |
| Cordyceps | 5% |
| Reishi | 5% |
| Truffle Powder | 0.5% |

TABLE 8

Eighth Illustrative Embodiment

| Ingredient | Percentage |
| --- | --- |
| Chocolate, between 60% and 90% cacao | 60% or more |
| Pine Pollen | 1% to 20% |
| Pine Bark Extract | 1% to 10% |
| Cordyceps | 1% to 20% |
| Reishi | 1% to 20% |
| Turkey Tail | 1% to 20% |
| Lion's Mane | 1% to 20% |
| Truffle Powder | 1% to 20% |

TABLE 9

Ninth Illustrative Embodiment

| Ingredient | Percentage |
| --- | --- |
| Chocolate, 75% cacao, sugar, vanilla, lecithin | 75% |
| Pine Pollen | 8.5% |
| Pine Bark Extract | 2% |
| Cordyceps | 4% |
| Reishi | 4% |
| Turkey Tail | 3% |
| Lion's Mane | 3% |
| Truffle Powder | 0.5% |

In any of the illustrative embodiments listed in the tables above, any other medicinal mushrooms may be used in lieu of (or in addition to) any of the listed mushrooms. Any DHEA boosting compound may be used in lieu of (or in addition to) pine pollen and truffle powder. Chocolate may contain any other ingredients in addition to cacao. Any other ingredient or ingredients with known or suspected health benefit related to stem cells or other body functions may be included in one or more embodiments. Embodiments may combine or interchange the elements and percentages in any of the tables in any desired manner. Percentages are approximate.

Includes a method of supporting cardiovascular health, improving sexual performance and sexual health, and improving athletic performance by administering a therapeutic amount of the compound to a subject.

While the invention herein disclosed has been described by means of specific embodiments and applications thereof, numerous modifications and variations could be made thereto by those skilled in the art without departing from the scope of the invention set forth in the claims.

What is claimed is:

1. A stem cell boosting composition comprising:
   chocolate comprising cacao, wherein a concentration by weight of said cacao in said stem cell boosting composition comprises at least 50% by weight of a total weight of said stem cell boosting composition,
      wherein said chocolate is in a concentration of at least 70% by weight of the total weight of the stem cell boosting composition; and,
      wherein said cacao is in a concentration by weight of between 60% and 90% of the weight of said chocolate;
   one or more DHEA boosting compounds in concentration between 2% and 38% by weight of the total weight of the stem cell boosting composition; and,
   one or more mushroom extracts in concentration between 2% and 38% by weight of the total weight of the stem cell boosting composition.

2. The stem cell boosting composition of claim 1, further comprising
   vitamin B12 in a concentration between 0.0001% and 5% by weight of the total weight of the stem cell boosting composition.

3. The stem cell boosting composition of claim 1, further comprising
   said chocolate in a concentration of about 75% by weight of the total weight of the stem cell boosting composition.

4. The stem cell boosting composition of claim 1, wherein said one or more DHEA boosting compounds comprise pine pollen, truffle powder, or any combination thereof.

5. The stem cell boosting composition of claim 1, wherein said chocolate further comprises sugar, vanilla and soy lecithin.

6. The stem cell boosting composition of claim 1, further comprising pine bark extract.

7. The stem cell boosting composition of claim 6, further comprising
   vitamin B12 in a concentration between 0.0001% and 5% by weight of the total weight of the stem cell boosting composition.

8. The stem cell boosting composition of claim 1, wherein said one or more mushroom extracts comprise extracts of one or more medicinal mushrooms.

9. The stem cell boosting composition of claim 1, wherein said one or more mushroom extracts comprise extracts of cordyceps, reishi, turkey tail, lion's mane, chaga, agarikon, maitake, or any combination thereof.

10. The stem cell boosting composition of claim 1, wherein
    said cacao is in concentration by weight of about 73% of a weight of said chocolate in said stem cell boosting composition.

11. The stem cell boosting composition of claim 1, further comprising
    said cacao in a concentration by weight between 70% and 75% of a weight of said chocolate in said stem cell boosting composition;
    pine pollen in a concentration between 1% and 20% by weight of the total weight of the stem cell boosting composition;
    cordyceps in a concentration between 1% and 20% by weight of the total weight of the stem cell boosting composition;

reishi in a concentration between 1% and 20% by weight of the total weight of the stem cell boosting composition; and, truffle powder in a concentration between 1% and 20% by weight of the total weight of the stem cell boosting composition.

12. The stem cell boosting composition of claim 1, further comprising said chocolate in a concentration of about 80% by weight of the total weight of the stem cell boosting composition, wherein said chocolate comprises said cacao in a concentration of about 75% of a weight of said chocolate in said stem cell boosting composition;

pine pollen in a concentration of about 9.5% by weight of the total weight of the stem cell boosting composition;

cordyceps in a concentration of about 5% by weight of the total weight of the stem cell boosting composition;

reishi in a concentration of about 5% by weight of the total weight of the stem cell boosting composition; and, truffle powder in a concentration of about 0.5% by weight of the total weight of the stem cell boosting composition.

13. The stem cell boosting composition of claim 1, further comprising pine pollen in a concentration between 1% and 20% by weight of the total weight of the stem cell boosting composition;

pine bark extract in a concentration between 1% and 20% by weight of the total weight of the stem cell boosting composition;

cordyceps in a concentration between 1% and 20% by weight of the total weight of the stem cell boosting composition;

reishi in a concentration between 1% and 20% by weight of the total weight of the stem cell boosting composition;

turkey tail in a concentration between 1% and 20% by weight of the total weight of the stem cell boosting composition;

lion's mane in a concentration between 1% and 20% by weight of the total weight of the stem cell boosting composition; and, truffle powder in a concentration between 1% and 20% by weight of the total weight of the stem cell boosting composition.

14. The stem cell boosting composition of claim 1, further comprising wherein said chocolate comprises said cacao in a concentration of between 60% and 90% of a weight of said chocolate in said stem cell boosting composition;

pine pollen in a concentration of between 1% and 20% by weight of the total weight of said stem cell boosting composition;

pine bark extract in a concentration of between 1% and 10% by weight of the total weight of said stem cell boosting composition;

cordyceps in a concentration of between 1% and 20% by weight of the total weight of said stem cell boosting composition;

chaga in a concentration of between 1% and 20% by weight of the total weight of said stem cell boosting composition;

truffle powder in a concentration of between 1% and 20% by weight of the total weight of said stem cell boosting composition; and, vitamin B12 in a concentration of between 0.01% and 5% by weight of the total weight of said stem cell boosting composition.

15. The stem cell boosting composition of claim 1, further comprising said chocolate in a concentration of about 75% by weight of the total weight of said stem cell boosting composition, wherein said chocolate comprises said cacao in a concentration of about 75% of a weight of said chocolate in said stem cell boosting composition;

pine pollen in a concentration of about 10% by weight of the total weight of said stem cell boosting composition;

pine bark extract in a concentration of about 2% by weight of the total weight of said stem cell boosting composition;

cordyceps in a concentration of about 10% by weight of the total weight of said stem cell boosting composition;

chaga in a concentration of about 2.4% by weight of the total weight of said stem cell boosting composition;

truffle powder in a concentration of about 0.5% by weight of the total weight of said stem cell boosting composition; and, vitamin B12 in a concentration of about 0.1% by weight of the total weight of said stem cell boosting composition.

16. A method of supporting cardiovascular health, improving sexual performance and sexual health, and improving athletic performance comprising:

administering to a subject a therapeutic amount of a stem cell boosting composition, wherein said stem cell boosting composition comprises chocolate comprising cacao, wherein a concentration by weight of said cacao in said stem cell boosting composition comprises at least 50% by weight of a total weight of said stem cell boosting composition, wherein said chocolate is in a concentration of at least 70% by weight of the total weight of the stem cell boosting composition; and, wherein said cacao is in a concentration by weight of between 60% and 90% of the weight of said chocolate;

one or more DHEA boosting compounds in concentration between 2% and 38% by weight of the total weight of the stem cell boosting composition; and, one or more mushroom extracts in concentration between 2% and 38% by weight of the total weight of the stem cell boosting composition.

* * * * *